United States Patent
Bruder et al.

(10) Patent No.: US 6,925,141 B2
(45) Date of Patent: Aug. 2, 2005

(54) METHOD FOR IMAGING IN THE COMPUTER TOMOGRAPHY OF A PERIODICALLY MOVED OBJECT TO BE EXAMINED AND CT DEVICE FOR CARRYING OUT THE METHOD

(75) Inventors: Herbert Bruder, Hoechstadt (DE); Thomas Flohr, Uehlfeld (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 120 days.

(21) Appl. No.: 10/667,477

(22) Filed: Sep. 23, 2003

(65) Prior Publication Data
US 2004/0114708 A1 Jun. 17, 2004

(30) Foreign Application Priority Data
Sep. 23, 2002 (DE) .......................................... 102 44 180

(51) Int. Cl.⁷ ................................................ A61B 6/03
(52) U.S. Cl. ................................ 378/8; 378/4; 378/901
(58) Field of Search ........................... 378/4, 8, 15, 19, 378/901

(56) References Cited

U.S. PATENT DOCUMENTS

| | | | |
|---|---|---|---|
| 5,079,697 A | * | 1/1992 | Chesler ...................... 382/280 |
| 6,266,553 B1 | | 7/2001 | Fluhrer et al. |
| 6,408,043 B1 | | 6/2002 | Hu et al. |
| 6,459,754 B1 | * | 10/2002 | Besson et al. ................. 378/4 |
| 6,556,697 B1 | | 4/2003 | Bruder et al. |
| 2005/0008116 A1 | * | 1/2005 | Nishide et al. ............... 378/20 |

FOREIGN PATENT DOCUMENTS

| | | |
|---|---|---|
| DE | 19740214 | 4/1999 |
| DE | 19842240 | 3/2000 |
| DE | 19842238 | 4/2000 |
| DE | 10063636 | 7/2001 |
| DE | 10159927 | 6/2003 |

* cited by examiner

*Primary Examiner*—David V Bruce
(74) *Attorney, Agent, or Firm*—Harness, Dickey & Pierce, P.L.C.

(57) ABSTRACT

A method is for imaging in computer tomography, in which a periodically moved object to be examined is scanned with the aid of a beam of rays coming from a focus. A two-dimensionally designed detector array generates output data which are filtered in a suitable way and back-projected in order to obtain at least one sectional image which represents the absorption values of the section of the object to be examined in a particular movement state. In the method, on the one hand, a weighting function which weights the spatial distance of a ray in question from the voxel in question is used for the back-projection. Further, on the other hand, a weighting function which represents the time difference from the examination area movement state to be represented in each case is also used.

24 Claims, 4 Drawing Sheets

METHOD FOR IMAGING IN THE COMPUTER TOMOGRAPHY OF A PERIODICALLY MOVED OBJECT TO BE EXAMINED AND CT DEVICE FOR CARRYING OUT THE METHOD

The present application hereby claims priority under 35 U.S.C. §119 on German patent application number DE 102 44 180.4 filed Sep. 23, 2002, the entire contents of which are hereby incorporated herein by reference.

FIELD OF THE INVENTION

The invention generally relates to a method for imaging in computer tomography. Preferably, it relates to one in which a periodically moved object to be examined is scanned with the aid of a beam of rays coming from a focus and a two-dimensionally designed detector array, wherein the output data which are determined are filtered in a suitable way and back-projected in order to obtain at least one sectional image which represents the absorption values of the section of the object to be examined in a particular movement state. The invention furthermore generally relates to a CT device; preferably one which is suitable for carrying out the method.

BACKGROUND OF THE INVENTION

Methods for static objects have in principle been disclosed under the term "3-D filtered back-projection". A disadvantage with these methods is that redundant data which result from spiral scans with a small incremental table feed, owing to multiple exposure of the same voxel, are not used. The consequence of this is that the radiation dose administered to the object to be examined is used only incompletely for the imaging. There are also problems in connection with carrying out image reconstruction methods in such a way that a large number of provisional images are calculated by "2D filtered back-projection" from output data which come from focal track sections that are insufficient for the image reconstruction per se; only in a second step are the provisional images reformatted to form a definitive sectional image. These 2D methods are less useful for detector arrays with a large width, i.e. a large extent in the direction of the system axis, because an extremely large number of provisional images then need to be processed, which is problematic even when a large computing power is available.

Cardio CT devices are in principle also generally known which produce sectional recordings of periodically moved objects to be examined, such as the human heart, by registering the movement phases of the heart and by only using data which correlate with particular movement phases or movement states to produce the sectional images. A disadvantage with the known cardio CT devices, however, is that they are only usable for detectors with a comparatively small number of rows, or a small extent of the detector in the system axis direction, since they do not take into account the conical ray profile in the object to be examined.

Reference will be made to the Applicant's German patent application DE 101 59 927.7, not yet published at the priority date of the present application and the contents of which are incorporated by reference herein in their entirety, which describes a similar method and CT device but which relates only to the imaging of static objects to be examined. The disclosure content of this application is fully included here.

SUMMARY OF THE INVENTION

It is an object of an embodiment of the invention to provide a method which, on the basis of 3D back-projection, makes it possible to increase the image quality and which can utilize redundant data of periodically moved objects to be examined with the correct phase to form sectional images.

According to an embodiment of the invention, an object may be achieved by a method and a CT device. Advantageous refinements are described in the detailed description.

Accordingly, the inventor provides an embodiment of a method for generating CT images of a periodically moving examination area, preferably the heart region of a living being, preferably of a patient, with at least the following method steps:

in order to scan a periodically moved object to be examined with a beam of rays coming from at least one focus and with a two-dimensionally designed detector array with a multiplicity of distributed detector elements for detecting the rays of the beam of rays, at least one focus is moved relative to the object to be examined on at least one focal track circumscribing the object to be examined with the detector array lying opposite, the detector elements of the detector array delivering output data which represent the attenuation of the rays when they pass through the object to be examined, movement data are simultaneously collected from the periodically moving examination area, in order to be able to assign the detector data and data resulting therefrom to the movement states, the output data are filtered, the filtered output data are three-dimensionally back-projected in order to generate at least one sectional image of a layer of the object to be examined having a layer thickness, each sectional image representing absorption values, obtained from the output data, of the voxel belonging to the layer of the object to be examined for the radiation of the beam of rays, on the one hand, a weighting function which weights the spatial distance of a ray in question from the voxel in question being used for the back-projection, and on the other hand, a weighting function which represents the time difference from the examination area movement state to be represented in each case also being used for the back-projection.

In a preferred embodiment of the method, the filtering is carried out in the direction of the tangent to the focal track belonging to the respective focal position. It has been shown that a particularly high image quality can be achieved with this filtering. The choice of this filter direction is based on the fact that the described 2D method based on provisional images, which allows a high image quality, could so to speak be converted into a 3D method if the focal track sections on which the calculation of provisional images is based were to be shortened so much that they can then be covered in a single projection, whose data are then filtered in the direction of the tangent to the focal track, and that it may be expected that such a 3D method would then allow as good an image quality compared with the 2D method.

The method according to an embodiment of the invention can then be implemented in a particularly straightforward way if a conversion of the output data obtained in the form of rays $P(\alpha,\beta,q)$ in a fan-ray geometry into parallel data available in the form of rays $P(\theta,\beta,q)$ ("azimuthal rebinning") or $P(\theta,p,q)$ ("complete rebinning", i.e. azimuthal and radial "rebinning") in a parallel-ray geometry is carried out before the filtering. In this case, referring to FIG. 3, $\alpha$ is the focal angle, $\beta$ is the fan angle, q is the row index of the detector system corresponding to the z coordinate, $\theta = \alpha + \beta$ is the parallel fan angle, $p = R_F \sin(\beta)$ is the parallel coordinate corresponding to the ray distance from the rotation axis (system axis), and $R_F$ is the radius of the focal track.

According to a preferred embodiment of the invention, back-projection of the parallel data is carried out in such a way that the sum $$P_{x,y,z}(\theta) = \sum_k \sum_q h_z\left(d_{x,y,z}\left(\theta + k\pi, \left\{\begin{array}{c}\tilde{p}\\ \tilde{\beta}\end{array}\right\}, q\right)\right) \cdot$$

$$h_{phase}(t(\theta + k\pi) - c_R(k)) \cdot P\left(\theta + k\pi, \left\{\begin{array}{c}\tilde{p}\\ \tilde{\beta}\end{array}\right\}, q\right)$$

is formed in the course of the back-projection for each voxel (x,y,z) for each $\theta \in [0,\pi[$ for the rays $P(\theta+k\pi, \beta, q)$ or $P(\theta+k\pi, \tilde{p}, q)$ whose projection along the system axis passes through (x,y), where x,y,z are the coordinates of the respective voxel, k is an integer corresponding to the number of half-circuits of the focus which are involved in the reconstruction, $\tilde{p}$ are the parallel coordinates of those rays whose projections along the system axis pass through the coordinates (x,y) of the respective voxel (x,y,z), $\tilde{\beta}$ are the fan angles of those rays whose projections along the system axis pass through the coordinates (x,y) of the respective voxel (x,y,z), $h_l$ is a weighting function determining the layer thickness of the layer of the object to be examined which is represented in the sectional image being produced, d is a function which is equal to the distance of the respective ray from the corresponding voxel (x,y,z) or depends on the distance of the respective ray from the corresponding voxel (x,y,z), and $h_{phase}$ is a weighting function relating to the time difference t of the projection $P(\theta+k\pi, \beta, q)$ or $P(\theta+k\pi, \tilde{p}, q)$ from a movement state, $c_R(k)$ representing a time position which determines the periodic movement state of an examination area, preferably an assigned heart cycle.

The notation $$\left\{\begin{array}{c}\tilde{p}\\ \tilde{\beta}\end{array}\right\}$$

here expresses the fact that the summation may be carried out selectively for rays obtained by azimuthal "rebinning" or by complete "rebinning", the filtering tangentially to the focal track being filtering in the $\beta$ direction in the case of azimuthal "rebinning" and filtering in the p direction in the case of complete "rebinning".

The summation over both k and q then guarantees that all rays passing through the same voxel are taken into account, and the radiation dose delivered to the object to be examined is therefore fully utilized.

In a particularly preferred embodiment, the sum $$P_{x,y,z}(\theta) = $$

$$\frac{1}{H} \sum_k \sum_q h_z\left(d_{x,y,z}\left(\theta + k\pi, \left\{\begin{array}{c}\tilde{p}\\ \tilde{\beta}\end{array}\right\}, q\right)\right) \cdot h_{phase}(t(\theta + k\pi) - c_R(k)) \cdot$$

$$P\left(\theta + k\pi, \left\{\begin{array}{c}\tilde{p}\\ \tilde{\beta}\end{array}\right\}, q\right)$$

which is normalized to the sum H of the weights h $$H = \sum_k \sum_q h_z\left(d_{x,y,z}\left(\theta + k\pi, \left\{\begin{array}{c}\tilde{p}\\ \tilde{\beta}\end{array}\right\}, q\right)\right) \cdot h_{phase}(t(\theta + k\pi) - c_R(k))$$

is formed during the back-projection of the parallel data. This procedure allows a further improved image quality, since possible over-emphasis of voxels which have received more rays than other voxels is eliminated and corresponding artifacts are hence avoided. The CT value of the respective voxel is obtained by summation over θ.

The method according to an embodiment of the invention may for example be employed when, according to a variant of an embodiment of the invention, the focal track is a circular track (tomogram scan). According to a preferred variant of an embodiment of the invention, however, the focal track is a spiral track which is obtained by moving the focus on the circular track about the system axis and simultaneously carrying out a relative movement between the focus and the object to be examined in the direction of the system axis. Larger volumes of the periodically moved object to be examined may also readily be determined on the basis of such spiral scanning.

In the case of a tomogram scan, k=1 or k=2 normally applies for k. In the case of a spiral scan, k will be selected so that all rays in the projection angle θ belonging to the parallel coordinate p or to the fan angle β whose distance $d_{x,y,z}$ does not exceed a suitable threshold are recorded for the image reconstruction.

The present invention will become more fully understood from the detailed description of preferred embodiments given hereinbelow and the accompanying drawings which are given by way of illustration only, and thus are not limitative of the present invention, and wherein.

DETAILED DESCRIPTION OF THE PREFERRED EMBODIMENTS

Figure 1:
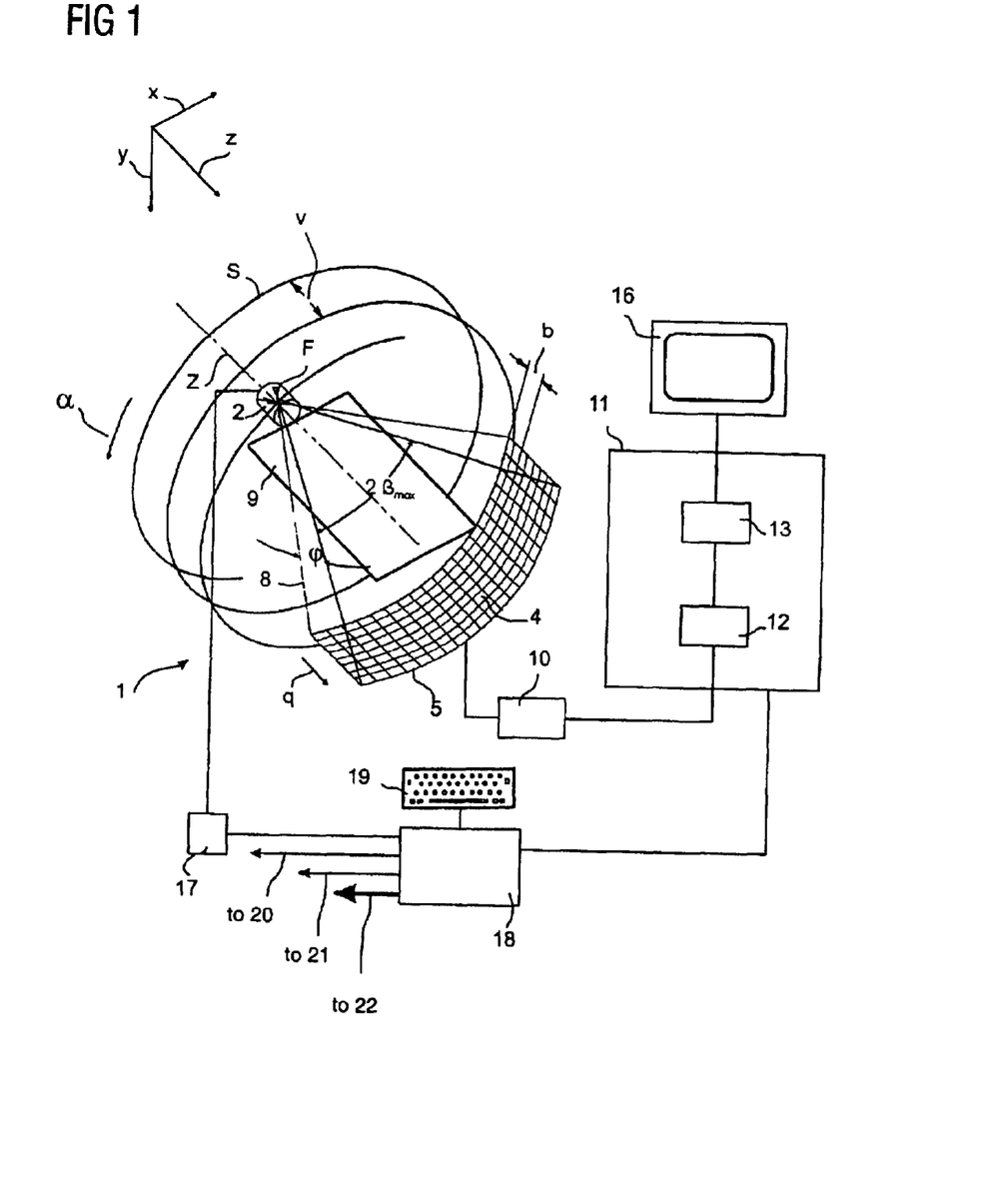
FIG. 1 illustrates a CT device having a plurality of rows of detector elements in a partly perspective and partly block-diagrammatic representation.
Figure 2:
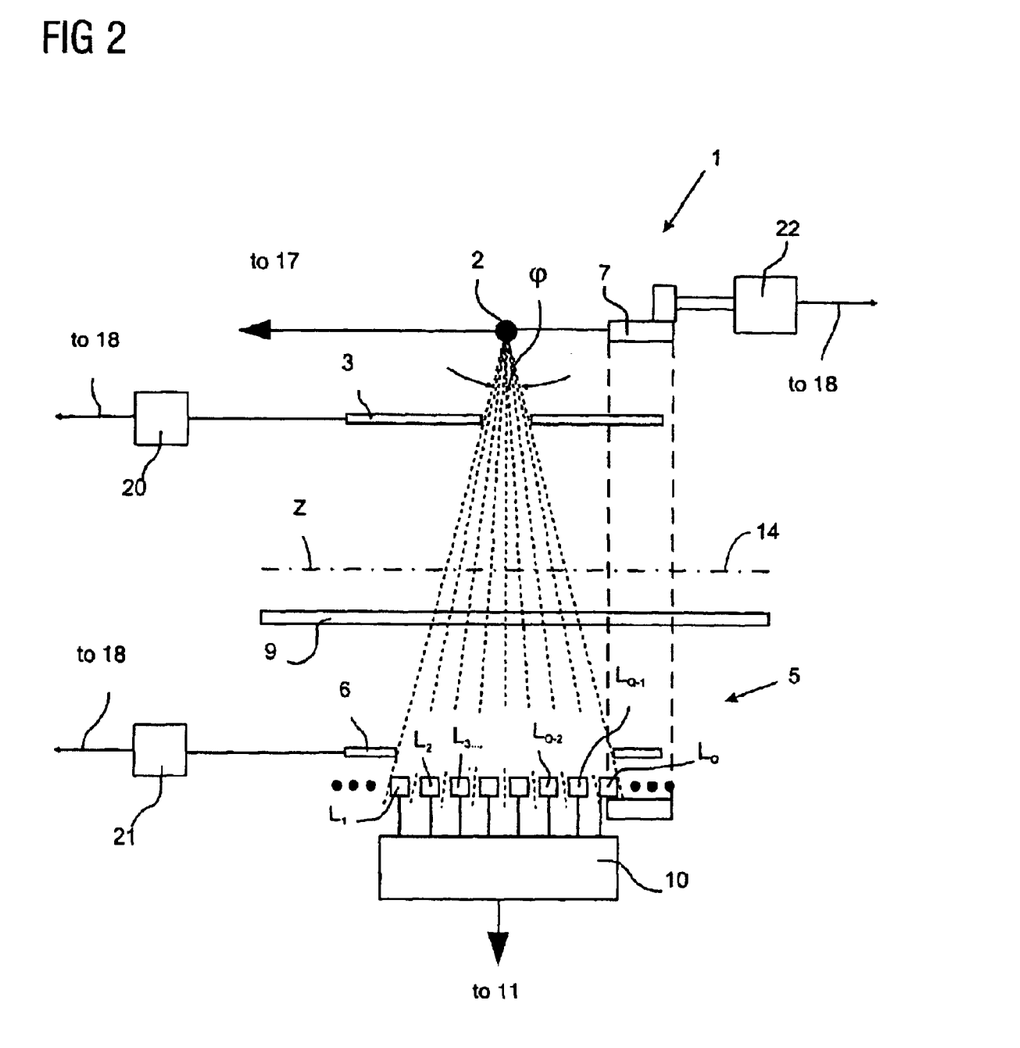
FIG. 2 illustrates a longitudinal section through the device according to FIG. 1.

FIGS. 1 and 2 represent a 3rd generation CT device suitable for carrying out the method according to an embodiment of the invention. Its measuring arrangement, denoted overall by 1, has an x-ray source, denoted overall by 2, with a source-side beam diaphragm 3 (FIG. 2) placed in front of it and a detector system 5 designed as a flat array of a plurality of rows and columns of detector elements—one of these is denoted by 4 in FIG. 1 —with a detector-side beam diaphragm 6 (FIG. 2) placed in front of it. Only eight rows of detector elements 4 are represented in FIG. 1 for the sake of clarity. As indicated by dots in FIG. 2, however, the detector system 5 has further rows of detector elements 4.

The x-ray source 2 with the beam diaphragm 3, on the one hand, and the detector system 5 with the beam diaphragm 6, on the other hand, as can be seen in FIG. 2, are fitted opposite one another on a rotary frame 7 in such a way that a pyramidal x-ray beam whose edge rays are denoted by 8, which comes from the x-ray source 2 during operation of the CT device and is stopped down by the adjustable beam diaphragm 3, strikes the detector system 5. In this case, the beam diaphragm 6 is adjusted to correspond with the x-ray beam cross section set by means of the beam diaphragm 3, in such a way as to expose only the area of the detector system 5 which can receive the x-ray beam directly. In the operating mode illustrated in FIGS. 1 and 2, these are eight rows of detector elements 4, which will be referred to below as the active rows. The further rows indicated by dots are covered by the beam diaphragm 6 and are therefore inactive.

Each row of detector elements 4 has a number K of detector elements, $\beta_k=\beta_1$ to $\beta_K$ being the channel index and a fan angle $\beta_k$ being assigned to each detector element. The fan angle of the central detector element is equal to zero; the fan angles of the two outermost detector elements are $\beta_1=+\beta_{max}$ and $\beta_K=-_{max}$.

The active rows $L_q$ of detector elements 4 are denoted by $L_1$ to $L_Q$ in FIG. 2, q=1 to Q being the row index, which corresponds so to speak to the z coordinate in the case of the exemplary embodiment being described.

The x-ray beam has the cone angle $\phi$ indicated in FIGS. 1 and 2, which is the aperture angle of the x-ray beam in a plane containing the system axis Z and the focus F. The aperture angle of the x-ray beam in a plane perpendicular to the system axis Z and containing the focus F (fan aperture angle) is $2\beta_{max}$ and is indicated in FIG. 1.

The rotary frame 7 can be set in rotation about a system axis denoted by Z, by means of a drive instrument 22. The system axis Z extends parallel to the z axis of a right-angled spatial coordinate system represented in FIG. 1.

The columns of the detector system 5 also extend in the direction of the z axis while the rows, whose width b is measured in the direction of the z axis and is for example 1 mm, extend transversely to the system axis Z or the z axis.

In order to be able to bring an object to be examined, for example a patient, into the beam path of the x-ray beam, a support device 9 is provided which can be displaced parallel to the system axis Z, i.e. in the direction of the z axis, so as to obtain synchronization between the rotation movement of the rotary frame 7 and the translation movement of the support device such that the ratio of translation speed to rotation speed is constant, this ratio being adjustable by selecting the intended value of the incremental feed v of the support device per revolution of the rotary frame.

It is hence possible for a volume of an object to be examined, lying on the support device 9, to be examined in the course of a volume scan; the volume scan may be carried out in the form of a spiral scan such that a multiplicity of projections from different projection directions are recorded by means of the measuring unit per revolution of the measuring unit 1, by simultaneous rotation of the measuring unit 1 and translation of the support device 9. During the spiral scan, the focus F of the x-ray source moves relative to the support device 9 on a spiral track denoted by S in FIG. 1. The spiral scan must extend over at least $\pi+2\beta_{max}$ in the $\alpha$ direction, in order to permit the complete reconstruction of one CT image per row of detector elements, although it may be arbitrarily longer within the technical limitations of the CT device.

Owing to the fact that there are a plurality of rows of detector elements 4, a volume of the object to be examined may nevertheless also be examined in the course of a so-called tomogram scan, in which no relative movement in the direction of the z axis takes place between the measuring unit 1 and the support device 9 (v=0). In the case of the tomogram scan, the size of the examined volume is hence determined by the number of active rows of detector elements 4. During a tomogram scan, the focus F moves on a circular focal track, which lies in a plane referred to below as the mid-plane.

The tomogram scan may be carried out in the form of a part-circuit or in the form of the full circuit, the part-circuit including a part-circuit interval of at least $\pi+2\beta_{max}$ (one half-circuit plus the fan aperture angle) which permits the complete reconstruction of a CT image, while a full scan comprises $2\pi$.

The measurement data read out in parallel from the detector elements of each active row of the detector system 5 during the spiral or tomogram scan, which correspond to the individual projections $P(\alpha, \beta, q)$ in a fan-ray geometry, are subjected to digital/analog conversion in a data processing unit 10, serialized and transmitted to an image computer 11.

After preprocessing of the measurement data in a preprocessing unit 12 of the image computer 11, the resulting datastream is sent to a sectional image reconstruction unit 13 which, from the measurement data, reconstructs sectional images of intended layers of the object to be examined on the basis of "filtered back-projection" by using a method according to an embodiment of the invention which is yet to be described in detail.

The CT images are made up of matricially assembled pixels (pixel=picture element), the pixels being assigned to the respective image plane, each pixel being assigned a CT number in Hounsfield units (HU) and the individual pixels being represented according to a CT-number/gray-value scale in a gray value corresponding to its respective CT number. Each pixel in this case illustrates a voxel (voxel=volume element) of the layer of the object to be examined illustrated in the CT image. Since measurement data corresponding to a plurality of layers of the object to be examined are available owing to the multiple-row nature of the detector system 5 and, where applicable, the spiral scan, 3D data are available which are subjected to 3D back-projection in the scope of an embodiment of the invention. In the end, 3D image data are available in the form of a three-dimensional matrix, for example with the axes x,y,z, each element of the matrix corresponding to one voxel (x,y,z) and containing the gray value corresponding to the associated CT number. Those elements of the three-dimensional matrix which have the same x,y or z value then respectively constitute a planar sectional image of the layer of the object to be examined corresponding to the relevant x,y or z value.

The images reconstructed by the sectional image reconstruction unit 13 are represented on a display unit 16 connected to the image computer 11, for example a monitor.

The x-ray source 2, for example an x-ray tube, is supplied by a generator 13 with the required voltages and currents, for example the tube voltage U. In order to be able to set them to the respectively required values, the generator unit 17 is assigned a control unit 18 with a keyboard 19, which allows the necessary settings to be made.

The other operation and control of the CT device is also carried out by way of the control unit 18 and the keyboard 19, which is illustrated by the fact that the control unit 18 is connected to the image computer 11.

Inter alia, it is possible to set the number Q of active rows of detector elements 4 and therefore the position of the beam diaphragms 3 and 6, for which the control unit 18 is connected to adjustment units 20 and 21 assigned to the beam diaphragms 3 and 6. It is also possible to set the rotation time τ which the rotary frame 7 requires for a full revolution, which is illustrated by the fact that the drive unit 22 assigned to the rotary frame 7 is connected to the control unit 18.

Although it is also possible in principle to carry out the method according to an embodiment of the invention in a fan-ray geometry, the described CT device is preferably operated in a mode in which the method according to an embodiment of the invention is carried out in a parallel-ray geometry.

Accordingly, the data obtained in a fan-ray geometry during the scan of the patient's body area relevant to the respective examination by spiral or tomogram scanning are first converted into a parallel-ray geometry, in a manner which is known per se, by a method generally referred to as "rebinning". This conversion is based on re-sorting of the data obtained in a fan-ray geometry, in such a way that rays from different projections recorded in a fan-ray geometry are taken and combined to form a projection in a parallel-ray geometry. In a parallel-ray geometry, data from an interval with the length π are sufficient in order to be able to reconstruct a complete image. In order to be able to obtain these data, data in a fan-ray geometry from an interval with the length $\pi+2\beta_{max}$ must nonetheless be available.

Figure 3:
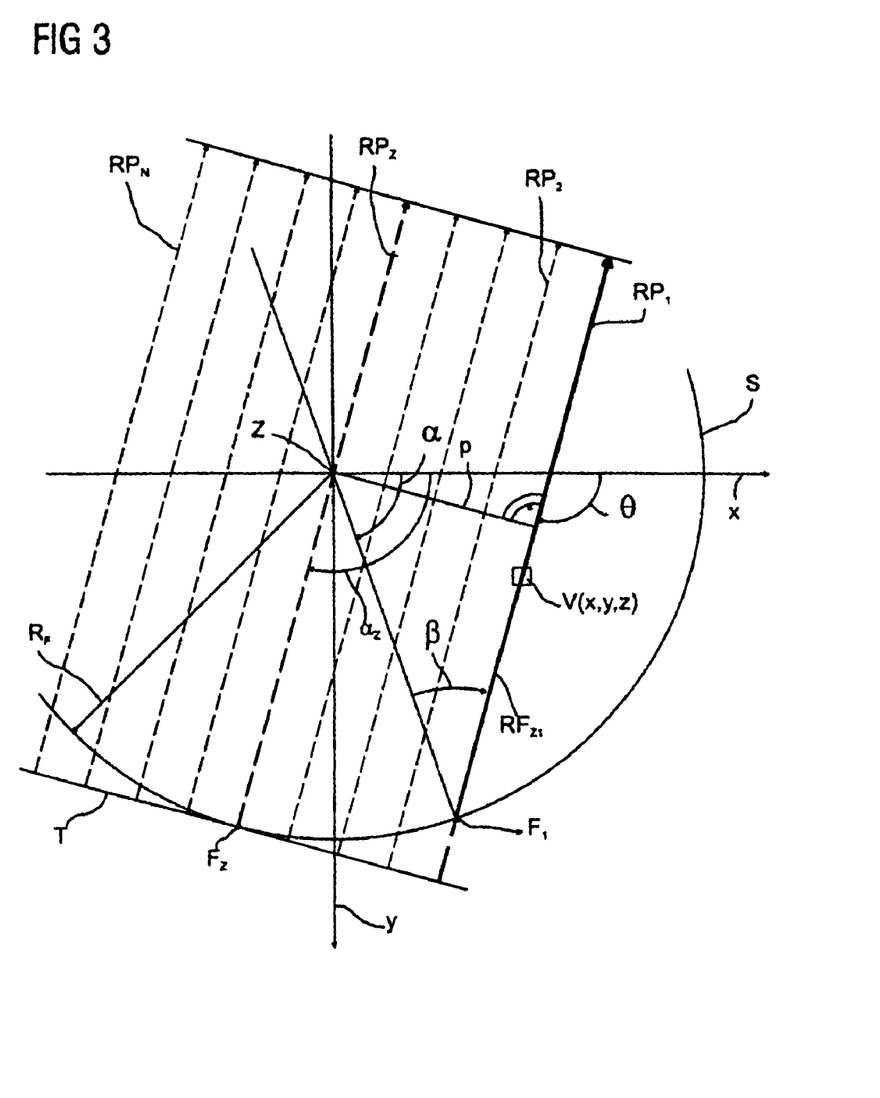
FIG. 3 illustrates a view illustrating the "rebinning"

A projection in a parallel-ray geometry is illustrated in FIG. 3. Accordingly, all n parallel rays $RP_1$ to $RP_N$ of this projection assume the parallel fan angle θ with respect to the x axis of the coordinate system represented in FIG. 3 and corresponding to that according to FIG. 1.

The conversion from a fan-ray geometry to a parallel-ray geometry will be explained below with the aid of the parallel ray $RP_1$, represented by a bold line in FIG. 3.

The parallel ray $RP_1$ originates from a projection obtained in a fan-ray geometry for the focal position $F_1$ lying on the focal track S. The central ray $RF_{z1}$i belonging to this projection in a fan-ray geometry and passing through the rotation axis 14, and therefore the z axis of the coordinate system, is also indicated in FIG. 3. The focal position $F_1$ corresponds to the focal angle $\alpha_1$; this is the angle formed between the x axis and the central ray $RF_{z1}$. With respect to the central ray $RF_{z1}$, the ray $RP_1$ has the fan angle β. It is therefore easy to see that the following applies for the parallel fan angle θ: $\theta=\alpha+\beta$.

The ray distance p from the rotation axis 14 or the z axis, measured at right angles to the respective parallel ray, is given by $p=R_F \sin(\beta)$.

As is made clear by the central ray RP, represented by an emboldened line in FIG. 3 and passing through the rotation axis 14 or the X axis, this ray is the central ray of a projection in a fan-ray geometry recorded in a fan geometry for the focal position $F_z$ at the focal angle $\alpha_z$. Since β=0 applies for the central ray of a projection recorded in a fan-ray geometry, it is clear that the following applies for the case of central rays:

Depending on whether azimuthal or complete "rebinning" is carried out, the parallel projections are in the form $P(\alpha,\beta,q)$ or in the form $P(\theta, p,q)$, where α is the focal angle,
β is the fan angle,
q is the row index of the detector system corresponding to the z coordinate,
θ=α+β is the parallel fan angle,
p=$R_F$ sin(β) is the parallel coordinate corresponding to the ray distance from the rotation axis (system axis), and
$R_F$ is the radius of the focal track.

In a first operating mode corresponding to a first embodiment of the method according to the invention, which can be selected by means of the keyboard 19, the described CT device works on the basis of projections obtained by azimuthal "rebinning". The data corresponding to these projections are filtered in the β direction in the case of azimuthal "rebinning", i.e. respectively in the direction of the tangent T belonging to the focal position of the central ray of the respective parallel projection (see FIG. 3), specifically by using one of the filter kernels which are conventional in computer tomography, for example the Shepp-Logan or Ramachandran-Lakshminarayanan kernel.

The parallel data filtered in this way are then back-projected in such a way that the sum $$P_{x,y,z}(\theta) = \sum_{k}\sum_{q} h_z(d_{x,y,z}(\theta+k\pi, \tilde{\beta}, q)) \cdot h_{phase}(t(\theta+k\pi)-c_R(k)) \cdot P(\theta+k\pi, \tilde{\beta}, q)$$

is formed in the course of the back-projection for each voxel (x,y,z) for each $\theta\in[0, \pi[$ for the rays $P(\theta+k\pi,\beta, q)$ whose projection along the system axis passes through (x,y), where x,y,z are the coordinates of the respective voxel,
k is an integer corresponding to the number of half-circuits of the focus which are involved in the reconstruction,
β are the fan angles of those rays whose projections along the system axis pass through the coordinates (x,y) of the respective voxel (x,y,z),
$h_z$ is a weighting function determining the layer thickness of the layer of the object to be examined which is represented in the sectional image being produced,
d is a function which is equal to the distance of the respective ray from the corresponding voxel (x,y,z) or depends on the distance of the respective ray from the corresponding voxel (x,y,z), and
$h_{phase}$ is a weighting function relating to the time difference t of the projection $P(\theta+k\pi,\beta,q)$ $P(\theta+k\pi,\tilde{p}, q)$ from a movement state,
$c_R(k)$ representing a time position which determines the periodic movement state of an examination area, preferably an assigned heart cycle.

Owing to the chosen filter direction and owing to the summation over both k and q, on the one hand "cone beam artifacts" are avoided and, on the other hand, all rays passing through a voxel (x,y,z) are taken into account with a view to high dose utilization. Furthermore, only rays which are correlated with that movement state of the object to be examined which is intended to be observed are taken into account by the weighting function $h_{phase}$, and measurements not correlated with it are suppressed.

The absorption value $\mu_{x,y,z}$ assigned to a voxel x,y,z is obtained by summation over θ over at least one half-circuit, i.e. by forming $$\mu_{x,y,z} = \sum_{\theta} P_{x,y,z}(\theta).$$

The CT number corresponding to the respective absorption value is determined from the absorption value in a conventional way.

In this case, various weighting functions h and various functions d can be set by means of the keyboard 19.

For example, a triangle or trapezium function may be suitable as the weighting function h.

The distance of the respective parallel ray from the voxel x,y,z or, instead of this, for example the z (axial) component of this distance may be set as the function d.

In a variant of the first operating mode described above, the sum $$P_{x,y,z}(\theta) =$$

$$\frac{1}{H}\sum_{k}\sum_{q} h_z(d_{x,y,z}(\theta + k\pi, \tilde{\beta}, q)) \cdot h_{phase}(t(\theta + k\pi) - c_R(k)) \cdot P(\theta + k\pi, \tilde{\beta}, q)$$

which is normalized to the sum H of the weights $h_z$ and $h_{phase}$ $$H = \sum_{k}\sum_{q} h_z(d_{x,y,z}(\theta + k\pi, \tilde{\beta}, q)) \cdot h_{phase}(t(\theta + k\pi) - c_R(k))$$

is formed for the back-projection of the parallel data. This permits a further improved image quality since possible over-emphasis of voxels which are "illuminated", i.e. struck by rays, in a plurality of half-circuits is eliminated and corresponding artifacts are hence avoided. This redundancy occurs in spiral scans whenever the relative displacement taking place per full circuit of the measuring arrangement is so small (small pitch) that voxels are irradiated several times.

An operating mode corresponding to another embodiment of the method according to the invention, which can be selected via the keyboard 19, differs from the first operating mode in that the described CT device works not on the basis of projections obtained by azimuthal "rebinning", but on the basis of projections obtained by complete "rebinning". The data corresponding to these projections are filtered in the p direction in the case of complete "rebinning", i.e. likewise respectively in the direction of the tangent T belonging to the focal position of the central ray of the respective parallel projection (see FIG. 3).

Accordingly, the sum $$P_{x,y,z}(\theta) =$$

$$\sum_{k}\sum_{q} h_z(d_{x,y,z}(\theta + k\pi, \tilde{p}, q)) \cdot h_{phase}(t(\theta + k\pi) - c_R(k)) \cdot P(\theta + k\pi, \tilde{p}, q)$$

is formed in the course of the back-projection for the parallel data filtered in this way, $\tilde{p}$ being the parallel coordinates of those rays whose projections along the system axis pass through the coordinates (x,y) of the respective voxel (x,y,z).

Also in the case of the second operating mode, in a variant, a sum which is normalized to the sum H of the weights $h_z$ and $h_{phase}$ $$H = \sum_{k}\sum_{q} h_z(d_{x,y,z}(\theta + k\pi, \tilde{p}, q)) \cdot h_{phase}(t(\theta + k\pi) - c_R(k))$$

is formed for the back-projection of the parallel data, namely the sum $$P_{x,y,z}(\theta) =$$

$$\sum_{k}\sum_{q} h_z(d_{x,y,z}(\theta + k\pi, \tilde{p}, q)) \cdot h_{phase}(t(\theta + k\pi) - c_R(k)) \cdot P(\theta + k\pi, \tilde{p}, q).$$

In the case of the first and second operating modes described above, a functionality of the method according to an embodiment of the invention is provided in which all rays whose projection along the rotation axis 14 or the z axis passes through x,y are taken into account in relation to a voxel (x,y,z). How and to what extent these rays are taken into account will be determined by the weighting function $h_z$ and the function d.

Figure 4:
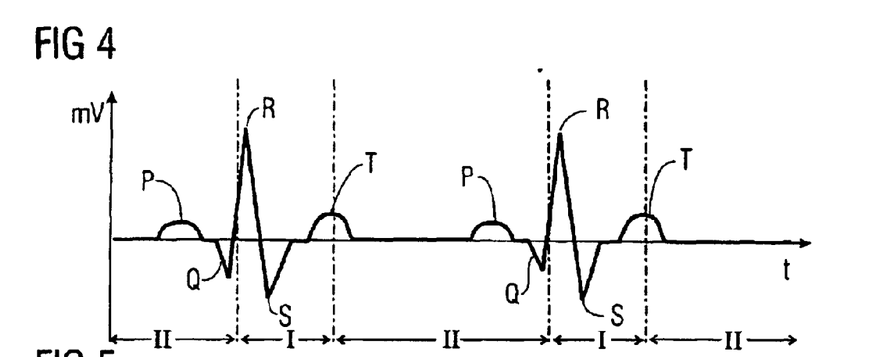
FIG. 4 illustrates a typical ECG of a human heart.
Figure 5:
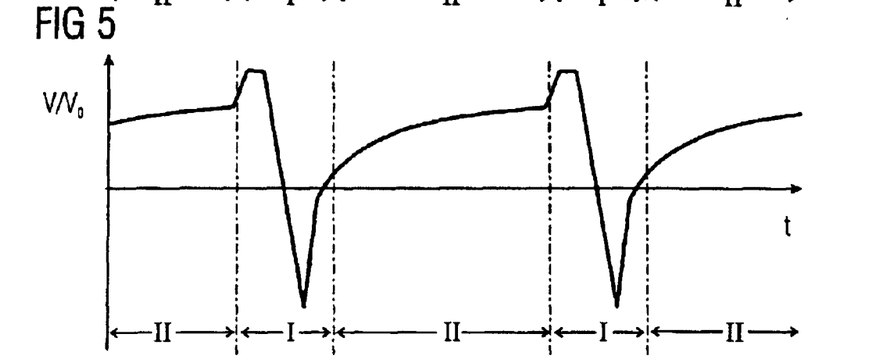
FIG. 5 illustrates a movement state of the heart, represented by relative volume change and correlated with the ECG in FIG. 4.
Figure 6:
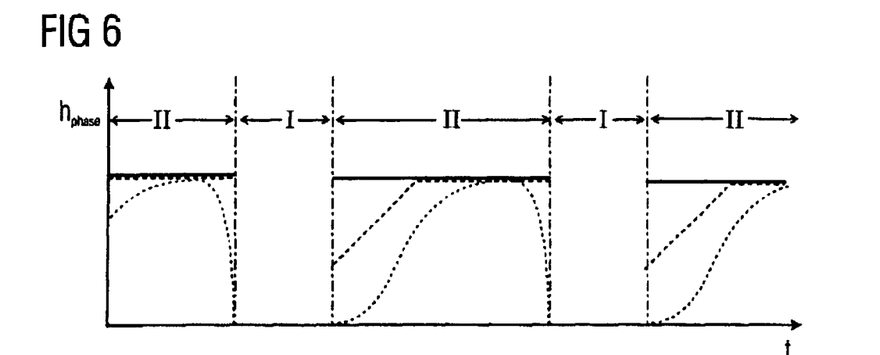
FIG. 6 illustrates the time profile of the weighting function $h_{phase}$ correlated with FIGS. 4 and 5.

FIGS. 4 to 6 show the time correlation between a patient's schematically represented ECG recording in FIG. 4, with the well-known typical profile over the atrial part with P wave and PQ interval, followed by the ventricular part with the QRS complex, ST interval, T wave and U wave. In this representation, only the P wave, QRS complex and T wave are highlighted as characteristic.

This typical and periodic ECG profile is correlated with particular movement states of the heart, which are represented in FIG. 5 with synchronous timing by plotting the relative volume change $V/V_0(t)$ of the heart. If this profile is roughly divided into two phases, then a movement phase I and a resting phase II are found. According to an embodiment of the invention, the CT recordings should respectively correspond to a particular phase so that, according to the respective phases, the weighting function $h_{phase}$ whose profile is represented in FIG. 6 guarantees that only information pertaining to this particular movement situation is in fact used for the imaging. Since it may be assumed that only minor movement takes place over a relatively long time span, namely the resting phase II of the heart, the entire resting phase II may, for example, be weighted heavily while the movement phase I is weighted lightly, as can be seen from FIG. 6. The bold line in FIG. 6 shows such a profile of the weighting function $h_{phase}$ with only two different values 1 and 0.

Alternatively, however, it is also possible to take into account the actual relative volume change and therefore the movement state in the heart, if, as represented in the profile of the weighting function $h_{phase}$ represented by dashes, different and more finely differentiated weightings are introduced depending on the extent of the resting of the heart. Furthermore, a weighting function which decreases with the time difference from a predetermined movement state may be chosen. This is represented, for example, by the dotted profile of the weighting function.

The CT device, however, may also have other operating modes selectable via the keyboard 19, which correspond to those described above with the difference that the theoretical ray passing through the respective voxel (x,y,z) is determined for a given focal position, and then only those rays which can actually make a contribution to the sum, both with reference to their position and with reference to the movement state of the relevant object to be examined which is of interest, are included in the summation in the course of the back-projection by taking into account the weighting functions $h_z$ and $h_{phae}$ and the function d.

In the case of the described exemplary embodiments, the relative movement between the measuring unit 1 and the support device 9 is respectively achieved by displacing the support device 9. It is, however, also possible in the scope of the invention to leave the support device 9 positionally fixed and to displace the measuring unit 1 instead of it. It is furthermore possible in the scope of the invention to generate the required relative movement by displacing both the measuring unit 1 and the support device 9.

The conical x-ray beam has a rectangular cross section in the case of the described exemplary embodiment. Other cross-sectional geometries, however, are also possible in the scope of the invention.

Third-generation CT devices are employed in connection with the exemplary embodiments described above, i.e. the x-ray source and the detector system are moved together about the system axis during the imaging. The invention, however, may also be employed in connection with fourth-generation CT devices, in which only the x-ray source is moved about the system axis and it interacts with a stationary detector ring, so long as the detector system is a multiple-row array of detector elements.

The method according to an embodiment of the invention may also be employed in fifth-generation CT devices, i.e. CT devices in which the x-radiation does not come from just one focus, but from a plurality of foci of one or more x-ray sources which are moved about the system axis, so long as the detector system has a multiple-row array of detector elements.

The CT devices used in connection with the exemplary embodiments described above have a detector system with detector elements arranged in the manner of an orthogonal matrix. The invention, however, may also be employed in connection with CT devices whose detector system has a flat-arranged array with detector elements in a different way.

The exemplary embodiments described above relate to the medical use of the method according to the invention. The invention, however, may also be used outside medicine, for example for the material examination of periodically moving machines or machine elements.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating CT images of a periodically moving examination area, comprising:

moving at least one focus, in order to scan a periodically movable object to be examined with a beam of rays coming from the at least one focus and with a two-dimensionally designed detector array with a multiplicity of distributed detector elements for detecting the rays of the beam of rays, relative to the object to be examined on at least one focal track circumscribing the object to be examined with the detector array lying opposite, wherein the detector elements of the detector array are adapted to deliver output data representing an attenuation of the rays when passed through the periodically movable object;

simultaneously collecting movement data upon movement of the movable object, to enable assigning of detector data and data resulting therefrom to movement states;

filtering the output data;

three-dimensionally back-projecting the filtered output data to generate at least one sectional image of a layer of the object to be examined having a layer thickness, wherein each sectional image represents absorption values, obtained from the output data, of the voxel belonging to the layer of the object to be examined for the radiation of the beam of rays, wherein a weighting function, for weighting the spatial distance of a ray in question from the voxel in question, is used for the back-projecting, and wherein a weighting function, representing a time difference from the examination area movement state to be represented is also used for the back-projecting.

2. The method as claimed in claim 1, wherein the filtering is carried out in the direction of a tangent to the focal track belonging to the respective focal position.

3. The method as claimed in claim 1, wherein a conversion of the output data, obtained in the form of rays $P(\alpha,\beta,q)$ in a fan-ray geometry into parallel data available in the form of at least one of rays $P(\theta, \beta,q)$ and $P(\theta,p,q)$ in a parallel-ray geometry, is carried out before the filtering, wherein $\alpha$ is the focal angle, $\beta$ is the fan angle, q is the row index of the detector system corresponding to the z coordinate, $\theta=\alpha+\beta$ is the parallel fan angle, $p=R_F \sin(\beta)$ is the parallel coordinate corresponding to the ray distance from the rotation axis (system axis), and $R_F$ is the radius of the focal track.

4. The method as claimed in claim 3, wherein the back-projecting of the parallel data is carried out in such a way that the sum $$P_{x,y,z}(\theta) = \sum_k \sum_q h_z\left(d_{x,y,z}\left(\theta+k\pi, \left\{\begin{array}{c}\tilde{p}\\ \tilde{\beta}\end{array}\right\}, q\right)\right) \cdot$$

$$h_{phase}(t(\theta+k\pi) - c_R(k)) \cdot P\left(\theta+k\pi, \left\{\begin{array}{c}\tilde{p}\\ \tilde{\beta}\end{array}\right\}, q\right)$$

is formed in the course of the back-projecting for each voxel (x,y,z) for each $\theta \in [0,\pi[$ for the rays $P(\theta+k\pi,\beta, q)$ or $P(\theta+k\pi, \tilde{p}, q)$ whose projection along the system axis passes through (x,y), wherein x,y,z are the coordinates of the respective voxel, k is an integer corresponding to the number of half-circuits of the focus which are involved in the reconstruction, $\tilde{p}$ are the parallel coordinates of those rays whose projections along the system axis pass through the coordinates (x,y) of the respective voxel (x,y,z), $\tilde{\beta}$ are the fan angles of those rays whose projections along the system axis pass through the coordinates (x,y) of the respective voxel (x,y,z), $h_z$ is a weighting function determining the layer thickness of the layer of the object to be examined which is represented in the sectional image being produced, d is a function which is equal to the distance of the respective ray from the corresponding voxel (x,y,z) or depends on the distance of the respective ray from the corresponding voxel (x,y,z), and $h_{phase}$ is a weighting function relating to the time difference of the projection $P(\theta+k\pi,\beta, q)$ or $P(\theta+k\pi, \tilde{p}q)$ from a movement state, $c_R(k)$ representing a time position which determines the periodic movement state of an examination area, preferably an assigned heart cycle.

5. The method as claimed in claim 4, wherein the sum $$P_{x,y,z}(\theta) = \frac{1}{H}\sum_k \sum_q h_z\left(d_{x,y,z}\left(\theta+k\pi, \left\{\begin{array}{c}\tilde{p}\\ \tilde{\beta}\end{array}\right\}, q\right)\right) \cdot$$

$$h_{phase}(t(\theta+k\pi) - c_R(k)) \cdot P\left(\theta+k\pi, \left\{\begin{array}{c}\tilde{p}\\ \tilde{\beta}\end{array}\right\}, q\right)$$

which is normalized to the sum H of the weights h $$H = \sum_k \sum_q h_z\left(d_{x,y,z}\left(\theta+k\pi, \left\{\begin{array}{c}\tilde{p}\\ \tilde{\beta}\end{array}\right\}, q\right)\right) \cdot h_{phase}(t(\theta+k\pi) - c_R(k))$$

is formed during the back-projection of the parallel data.

6. The method as claimed in claim 1, wherein the rays of each voxel in question are weighted during the back-projecting in such a way that rays striking the detector elements centrally are weighted relatively more heavily than rays striking at the edge.

7. The method as claimed in claim 1, wherein the focal track is a circular track.

8. The method as claimed in claim 1, wherein the focal track is a spiral track, obtained by moving the focus on the circular track about the system axis and simultaneously carrying out a relative movement between the focus and the object to be examined in the direction of the system axis.

9. The method as claimed in claim 1, wherein the detector elements are arranged distributed in rows and columns on the detector array.

10. A CT device for scanning a periodically movable object to be examined, with a beam of rays coming from at least one focus and with a two-dimensionally designed detector array with a multiplicity of distributed detector elements for detecting the rays of the beam of rays, the at least one focus being moved relative to the object to be examined on at least one focal track circumscribing the object to be examined with the detector array lying opposite, the CT device including means for detection of the movement state of the object to be examined, for collection of the detector data, for filtering and back-projection as claimed in claim 1.

11. The CT device as claimed in claim 10, wherein each of said means are implemented at least partially by at least one of programs and program modules.

12. The method of claim 1, wherein the method is for generating CT images of a heart region of a living being.

13. The method of claim 1, wherein the method is for generating CT images of a heart region of a patient.

14. The method as claimed in claim 2, wherein a conversion of the output data, obtained in the form of rays $P(\alpha, \beta, q)$ in a fan-ray geometry into parallel data available in the form of at least one of rays $P(\theta, \beta, q)$ and $P(\theta, p, q)$ in a parallel-ray geometry, is carried out before the filtering, wherein $\alpha$ is the focal angle, $\beta$ is the fan angle, q is the row index of the detector system corresponding to the z coordinate, $\theta = \beta + \beta$ is the parallel fan angle, $p = R_F \sin(\beta)$ is the parallel coordinate corresponding to the ray distance from the rotation axis (system axis), and $R_F$ is the radius of the focal track.

15. The method as claimed in claim 14, wherein the back-projecting of the parallel data is carried out in such a way that the sum $$P_{x,y,z}(\theta) = \sum_k \sum_q h_z\left(d_{x,y,z}\left(\theta + k\pi, \left\{\tilde{p}\atop\tilde{\beta}\right\}, q\right)\right) \cdot$$

$$h_{phase}(t(\theta + k\pi) - c_R(k)) \cdot P\left(\theta + k\pi, \left\{\tilde{p}\atop\tilde{\beta}\right\}, q\right)$$

is formed in the course of the back-projecting for each voxel (x, y, z) for each a $\theta \in [0, \pi[$ for the rays $P(\theta+k\pi, \beta, q)$ or $P(\theta+k\pi, \tilde{p}, q)$ whose projection along the system axis passes through (x,y), wherein x, y, z are the coordinates of the respective voxel, k is an integer corresponding to the number of half-circuits of the focus which are involved in the reconstruction, $\tilde{p}$ are the parallel coordinates of those rays whose projections along the system axis pass through the coordinates (x, y) of the respective voxel (x, y, z), $\tilde{\beta}$ are the fan angles of those rays whose projections along the system axis pass through the coordinates (x, y) of the respective voxel (x, y, z), $h_z$ is a weighting function determining the layer thickness of the layer of the object to be examined which is represented in the sectional image being produced, d is a function which is equal to the distance of the respective ray from the corresponding voxel (x, y, z) or depends on the distance of the respective ray from the corresponding voxel (x, y, z), and $h_{phase}$ is a weighting function relating to the time difference of the projection $P(\theta+k\pi, \beta, q)$ or $P(\theta+k\pi, \tilde{p},q)$ from a movement state, $c_R(k)$ representing a time position which determines the periodic movement state of an examination area, preferably an assigned heart cycle.

16. The method as claimed in claim 15, wherein the sum $$P_{x,y,z}(\theta) = \frac{1}{H}\sum_k \sum_q h_z\left(d_{x,y,z}\left(\theta + k\pi, \left\{\tilde{p}\atop\tilde{\beta}\right\}, q\right)\right) \cdot$$

$$h_{phase}(t(\theta + k\pi) - c_R(k)) \cdot P\left(\theta + k\pi, \left\{\tilde{p}\atop\tilde{\beta}\right\}, q\right)$$

which is normalized to the sum H of the weights h $$H = \sum_k \sum_q h_z\left(d_{x,y,z}\left(\theta + k\pi, \left\{\tilde{p}\atop\tilde{\beta}\right\}, q\right)\right) \cdot h_{phase}(t(\theta + k\pi) - c_R(k))$$

is formed during the back-projection of the parallel data.

17. The method as claimed in claim 2, wherein the focal track is a circular track.

18. The method as claimed in claim 2, wherein the focal track is a spiral track, obtained by moving the focus on the circular track about the system axis and simultaneously carrying out a relative movement between the focus and the object to be examined in the direction of the system axis.

19. The method as claimed in claim 5, wherein the focal track is a circular track.

20. The method as claimed in claim 5, wherein the focal track is a spiral track, obtained by moving the focus on the circular track about the system axis and simultaneously carrying out a relative movement between the focus and the object to be examined in the direction of the system axis.

21. The CT device of claim 10, wherein the CT device is for generating CT images of a heart region of a living being.

22. The CT device of claim 10, wherein the CT device is for generating CT images of a heart region of a patient.

23. A method for generating CT images, comprising:

scanning a periodically movable object to be examined with a beam of rays coming from at least one focus;

detecting the rays using a two-dimensionally designed detector array with a multiplicity of distributed detector elements, wherein the detector elements of the detector array are adapted to deliver output data representing an attenuation of the rays when passed through the periodically movable object;

simultaneously collecting movement data upon movement of the movable object, to enable assigning of detector data and data resulting therefrom to movement states;

filtering the output data;

three-dimensionally back-projecting the filtered output data to generate at least one sectional image of a layer of the movable object having a layer thickness, wherein each sectional image represents absorption values, obtained from the output data, of a voxel belonging to the layer of the movable object for the radiation of the beam of rays, wherein a weighting function, for weighting a spatial distance of a ray in question from a voxel in question, is used for the back-projecting, and wherein a weighting function, representing a time difference from an examination area movement state to be represented is also used for the back-projecting.

24. The method as claimed in claim 23, wherein the filtering is carried out in the direction of a tangent to the focal track belonging to the respective focal position.

* * * * *